United States Patent
Yagi

(10) Patent No.: US 9,791,392 B2
(45) Date of Patent: Oct. 17, 2017

(54) X-RAY FLUORESCENCE ANALYZER AND MEASUREMENT POSITION ADJUSTING METHOD THEREFORE

(71) Applicant: HITACHI HIGH-TECH SCIENCE CORPORATION, Tokyo (JP)

(72) Inventor: Isao Yagi, Tokyo (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 113 days.

(21) Appl. No.: 14/805,314

(22) Filed: Jul. 21, 2015

(65) Prior Publication Data
US 2016/0069827 A1  Mar. 10, 2016

(30) Foreign Application Priority Data
Sep. 9, 2014 (JP) .................. 2014-182919

(51) Int. Cl.
*G01N 23/223* (2006.01)
*G01N 23/22* (2006.01)

(52) U.S. Cl.
CPC .......... *G01N 23/223* (2013.01); *G01N 23/22* (2013.01); *G01N 2223/323* (2013.01)

(58) Field of Classification Search
CPC . G01N 23/22; G01N 23/223; G01N 2223/323
USPC ..................................... 378/44–50
See application file for complete search history.

(56) References Cited

U.S. PATENT DOCUMENTS

| | | | | |
|---|---|---|---|---|
| 6,345,086 B1 * | 2/2002 | Ferrandino | .......... | G01N 23/223 378/206 |
| 6,535,573 B2 * | 3/2003 | Yagi | ..................... | G01N 23/223 378/206 |
| 6,885,726 B2 * | 4/2005 | Uehara | ................ | G01N 23/223 378/145 |
| 7,970,101 B2 * | 6/2011 | Sakai | .................... | G01N 23/223 378/44 |
| 7,972,062 B2 * | 7/2011 | Nicolosi | .................. | G21K 7/00 378/205 |
| 8,000,439 B2 * | 8/2011 | Matoba | ................ | G01N 23/223 378/44 |
| 8,408,789 B2 * | 4/2013 | Takahara | ............. | G01N 23/223 378/195 |
| 8,611,493 B2 * | 12/2013 | Hasegawa | ............ | G01N 23/223 378/44 |
| 9,658,175 B2 * | 5/2017 | Hirose | ................. | G01N 23/223 |

FOREIGN PATENT DOCUMENTS

JP  2006-329944  12/2006

* cited by examiner

*Primary Examiner* — Allen C. Ho
(74) *Attorney, Agent, or Firm* — Brinks Gilson & Lione

(57) ABSTRACT

An X-ray fluorescence analyzer is provided with: a sample stage on which a sample subjected to an analysis is mounted; an X-ray source configured to irradiate the sample with primary X-rays; a detector configured to detect fluorescent X-rays emitted from the sample irradiated with the primary X-rays; an imaging unit configured to capture an image of a predetermined field-of-view area on the sample stage; a display unit configured to display the field-of-view area of the image captured by the imaging unit; and a pointer irradiation unit configured to irradiate the sample stage with a visible light at an irradiation position within an area that is outside the field-of-view area and near the field-of-view area.

10 Claims, 4 Drawing Sheets

X-RAY FLUORESCENCE ANALYZER AND MEASUREMENT POSITION ADJUSTING METHOD THEREFORE

CROSS-REFERENCE TO RELATED APPLICATION

This application claims priority from Japanese Patent Application No. 2014-182919, filed on Sep. 9, 2014, the entire subject matter of which is incorporated herein by reference.

BACKGROUND

1. Technical Field

The present disclosure relates to an X-ray fluorescence analyzer that is capable of detecting toxic substances or the like and which is used for screening products or measuring a film thickness of plating or the like and to a measurement position adjusting method for the apparatus.

2. Description of the Related Art

In a fluorescent X-ray analysis, a spectrum is acquired from energy by irradiating a sample with X-rays emitted from an X-ray source and detecting fluorescent X-rays which are characteristic X-rays emitted from the sample using an X-ray detector, and a qualitative analysis or a quantitative analysis of the sample or film thickness measurement is performed. Since samples can be rapidly analyzed in a non-destructive manner by the fluorescent X-ray analysis, the fluorescent X-ray analysis is widely used in the fields of process control, quality control, and the like. In recent years, high precision and high sensitivity of the fluorescent X-ray analysis are achieved, and thus trace measurement is enabled. In particular, the fluorescent X-ray analysis is expected to be spread as an analysis method of detecting toxic substances contained in materials, complex electronic parts, or the like.

In the X-ray fluorescence analyzer according to the related art, an operator sets a sample at a predetermined position on a sample stage and performs measurement. At this time, the setting position is irradiated with a laser beam or spotlight so as to mark the position at which the sample is set on the sample stage. The operator visually checks the position irradiated with a laser beam or spotlight, coarsely positions the sample, then observes the surface of the sample using an image from an imaging device such as a camera for observing a measurement position of the sample, finely positions the sample, and performs analysis or measurement on a desired position.

An example of the X-ray fluorescence analyzer according to the related is disclosed in JP-A-2006-329944.

The above-mentioned technique according to the related art may have the following problems.

That is, in a method of irradiating a setting position of a sample with a laser beam or spotlight and using the laser beam or the spotlight as a mark for coarse positioning as in the X-ray fluorescence analyzer according to the related art, since light such as the laser beam or the spotlight glares in an image from an imaging device in which the setting position is enlarged and displayed, there may be a problem in that it is difficult to observe the surface of a sample and a fine positioning operation becomes complicated.

SUMMARY

The present disclosure has been made in view of the above-described circumstances, and one of objects of the present disclosure is to provide an X-ray fluorescence analyzer in which coarse positioning can be easily performed and positioning light does not appear in an image in a fine positioning operation and a measurement position adjusting method thereof.

According to an exemplary embodiment of the present disclosure, there is provided an X-ray fluorescence analyzer including: a sample stage on which a sample subjected to an analysis is mounted; an X-ray source configured to irradiate the sample with primary X-rays; a detector configured to detect fluorescent X-rays emitted from the sample irradiated with the primary X-rays; an imaging unit configured to capture an image of a predetermined field-of-view area on the sample stage; a display unit configured to display the field-of-view area of the image captured by the imaging unit; and a pointer irradiation unit configured to irradiate the sample stage with a visible light at an irradiation position within an area that is outside the field-of-view area and near the field-of-view area.

According to another exemplary embodiment of the present disclosure, there is provided a measurement position adjusting method for an X-ray fluorescent analyzer of capturing an image a sample mounted on a sample stage using an imaging unit, displaying the image captured by the imaging unit on a display unit, positioning X-rays with which the sample is irradiated, and performing measurement or analysis of the sample, the method including: coarsely positioning the sample while irradiating the sample stage with a visible light at an irradiation position within an area that is outside the field-of-view area and near the field-of-view area; displaying the image captured by the imaging unit on the display unit; and finely positioning the sample based on the image displayed on the display unit after coarsely positioning the sample.

According to still another exemplary embodiment of the present disclosure, there is provided a measurement position adjusting method for an X-ray fluorescence analyzer having a sample stage, an imaging unit and a display unit, the method including: coarsely positioning a sample mounted on the sample stage while irradiating the sample stage with a visible light at an irradiation position within an area that is outside a field-of-view area and near the field-of-view area, the field-of-view area being an area on the sample stage in which an image is captured by the imaging unit; capturing the image of the field-of-view area by the imaging unit; displaying the image captured by the imaging unit on the display unit; and finely positioning the sample based on the image displayed on the display unit after coarsely positioning the sample.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

Hereinafter, an X-ray fluorescence analyzer and a measurement position adjusting method therefore according to a first embodiment of the disclosure will be described with reference to FIGS. 1 to 3.

Figure 1:
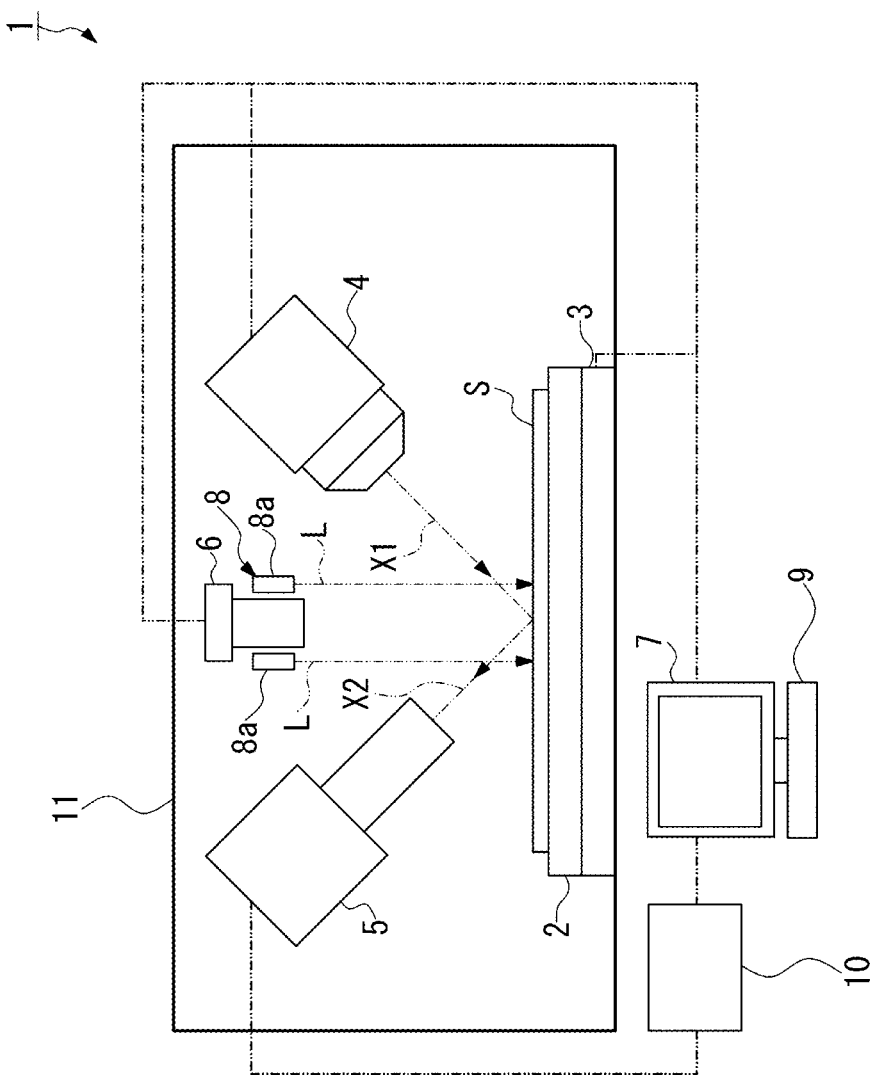
FIG. 1 is a diagram schematically illustrating an entire configuration of an X-ray fluorescence analyzer and a measurement position adjusting method thereof according to a first embodiment of the disclosure.
Figure 2:
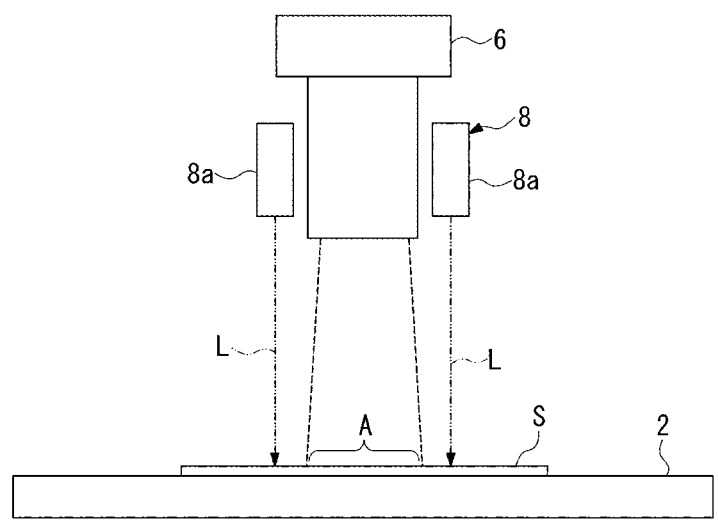
FIG. 2 is a front view illustrating an imaging unit, a pointer irradiation unit, and a sample stage in the first embodiment.
Figure 3:
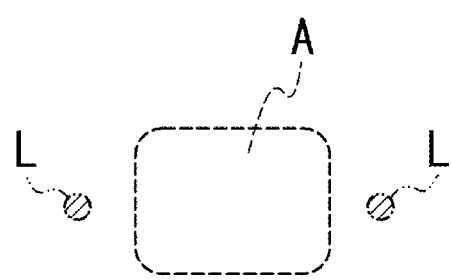
FIG. 3 is a plan view illustrating a positional relationship between a field-of-view area and visible light in the first embodiment.

As illustrated in FIGS. 1 to 3, an X-ray fluorescence analyzer 1 according to the first embodiment is provided with a sample stage 2 on which a sample S is mounted, a sample stage moving mechanism 3 configured to move the sample stage 2, an X-ray source 4 configured to irradiate the sample S with primary X-rays X1, a detector 5 configured to detect fluorescent X-rays X2 emitted from the sample S irradiated with the primary X-rays X1, an imaging unit 6 configured to capture an image a predetermined field-of-view area A on the sample stage 2, a display unit 7 configured to display the field-of-view area A of the image captured by the imaging unit 6, and a pointer irradiation unit 8 configured to irradiate an area in the vicinity of the field-of-view area A on the sample stage 2, which is an area other than the field-of-view area A displayed on the display unit 7, with a visible light beam L.

The pointer irradiation unit 8 is provided with a pair of laser beam irradiation mechanisms 8a configured to emit a laser beam of which the wavelength is in a visible light range as visible light L. For example, the laser beam irradiation mechanisms 8a may emit a red laser beam. The laser beam irradiation mechanism 8a irradiates areas, which are separated by a predetermined distance from both ends of the field-of-view area A, with the visible light beam L as a laser beam in the form of spots.

The imaging unit 6 is capable of changing the size of the field-of-view area A and the pointer irradiation unit 8 is capable of changing an irradiation position with the visible light L depending on the size of the field-of-view area A. That is, a pair of laser beam irradiation mechanisms 8a is provided with a mechanism (not illustrated) such as an optical system for adjusting a gap between visible light beams L and can adjust the gap between the visible light beams L so as to irradiate both sides of the field-of-view area A with a pair of visible light beams L to correspond to the changed size when the imaging unit 6 changes the size of the field-of-view area A.

The X-ray fluorescence analyzer 1 is provided with a control unit 9 configured to control the sample stage moving mechanism 3, the X-ray source 4, the detector 5, the imaging unit 6, and the pointer irradiation unit 8, an analyzer 10 connected to the detector 5 and configured to analyze a signal from the detector 5, and a housing 11 that accommodates the X-ray source 4, the detector 5, the imaging unit 6, the pointer irradiation unit 8, the sample stage 2, and the sample stage moving mechanism 3 therein.

The sample stage 2 is installed on the sample stage moving mechanism 3 as an XY stage on which the sample S can be placed and which can move at least in planar directions (X direction and Y direction).

The imaging unit 6 is an observation camera on which a CCD or the like is mounted and is installed above the sample stage 2 so as to image the sample S on the sample stage 2.

The pointer irradiation unit 8 is set to irradiate both sides of the field-of-view area A with the visible light beams L. That is, a pair of laser beam irradiation mechanisms 8a is installed on both sides of the imaging unit 6 and is disposed to irradiate the below sample stage 2 with a pair of visible light beams L as parallel light.

The X-ray source 4 is an X-ray tube capable of emitting primary X-rays X1 and serves to emit X-rays, which are generated by accelerating thermoelectrons generated from a filament (cathode) in the tube by a voltage applied between the filament (cathode) and a target (anode) and causing the thermoelectrons to collide with W (tungsten), Mo (molybdenum), Cr (chromium), or the like as the target, as the primary X-rays X1 from a window formed of a beryllium foil or the like.

The detector 5 is provided with a semiconductor detection device (for example, a Si (silicon) device which is a pin-structure diode) (not illustrated) which is installed in an X-ray incidence window (not illustrated) and serves to generate a current pulse corresponding to one X-ray photon when the one X-ray photon is incident. The instantaneous current value of the current pulse is in proportion to energy of incident characteristic X-rays. The detector 5 is set to convert and amplify the current pulse generated from the semiconductor detection device into a voltage pulse and to output the voltage pulse as a signal.

The analyzer 10 may be a pulse height analyzer (multichannel analyzer) that acquires a height of a voltage pulse from the signal and generates an energy spectrum.

The control unit 9 is provided with a computer including a processor and is connected to the display unit 17 and other components of the X-ray fluorescence analyzer 1. The control unit 9 controls the display unit 7 to display an analysis result on a screen of the display unit 7.

A measurement position adjusting method using the X-ray fluorescence analyzer 1 according to the first embodiment will be described below.

In the measurement position adjusting method according to the first embodiment, first, a coarse positioning operation of moving the sample stage 2 to move the sample S in the field-of-view area A is performed. At this time, as illustrated in FIG. 3, a pair of laser beam irradiation mechanisms 8a of the pointer irradiation unit 8 irradiates the sample stage 2 with a pair of visible light beams L (laser beams). The pair of visible light beams L is applied to both sides of the field-of-view area A in the vicinity of the field-of-view area A.

The coarse positioning operation is performed by moving the sample stage 2 using the sample stage moving mechanism 3 so as to locate the sample S between the pair of visible light beams L based on the pair of visible light beams L while visually checking the pair of visible light beams L. Then, a fine positioning operation is performed while watching the field-of-view area A displayed on the display unit 7 by the imaging unit 6 and then analysis or measurement is performed by emitting X-rays from the X-ray source 4.

As described above, since the X-ray fluorescence analyzer 1 according to the first embodiment is provided with the pointer irradiation unit 8 that irradiates an area in the vicinity of the field-of-view area A on the sample stage 2 as an area other than the field-of-view area A displayed on the display unit 7 with a visible light beam L, it is possible to perform a coarse positioning operation using the visible light beam L with which the sample stage 2 is irradiated as a mark. Thereafter, when a fine positioning operation is performed, the visible light beam L does not appear in the field-of-view area A displayed on the screen of the display unit 7 and thus an image of a sample surface without degradation in image quality or interference with visible light is displayed.

Since the pointer irradiation unit 8 emits a laser beam as a visible light beam L, the visibility is high and the coarse positioning operation is further facilitated.

Since the pointer irradiation unit 8 irradiates both sides of the field-of-view area A with the visible light beams L, it is possible to further easily perform the coarse positioning operation by positioning the sample between the two visible light beams L with which the sample stage 2 is irradiated.

The pointer irradiation unit 8 can change the irradiation position with the visible light beams L depending on the size of the field-of-view area A. Accordingly, even when the field-of-view area A is enlarged or reduced with a digital zoom, it is possible to easily perform the coarse positioning operation using the visible light beams L, which are changed to an irradiation position corresponding to the enlargement or reduction, as a mark.

X-ray fluorescence analyzers and measurement position adjusting methods thereof according to second and third embodiments of the disclosure will be described below with reference to FIGS. 4 to 7. In the following description of the embodiments, the same elements as described in the above-mentioned embodiment will be referenced by the same reference signs and description thereof will not be repeated.

Figure 4:
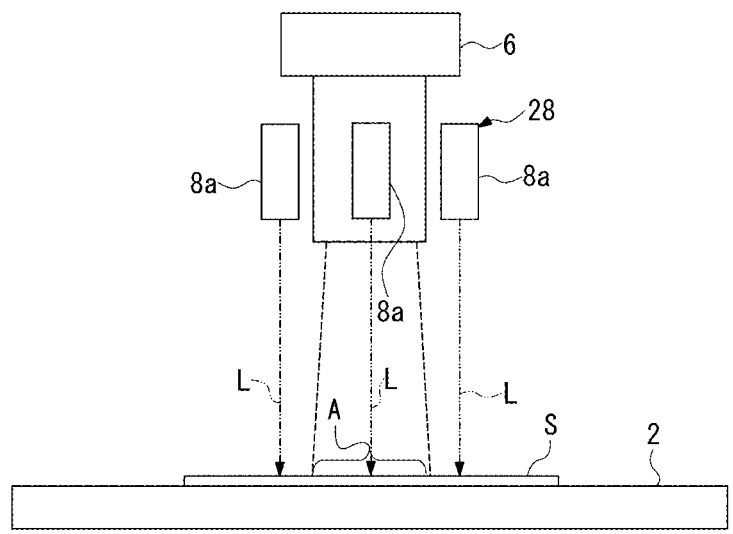
FIG. 4 is a front view illustrating an imaging unit, a pointer irradiation unit, and a sample stage in an X-ray fluorescence analyzer and a measurement position adjusting method thereof according to a second embodiment of the disclosure.
Figure 5A:
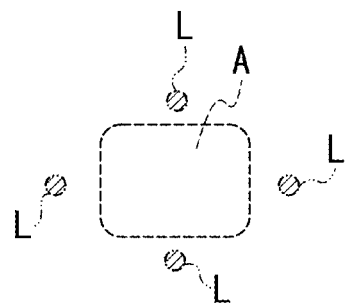
FIGS. 5A and 5B are plan views illustrating a positional relationship between a field-of-view area and visible light in the second embodiment.
Figure 5B:
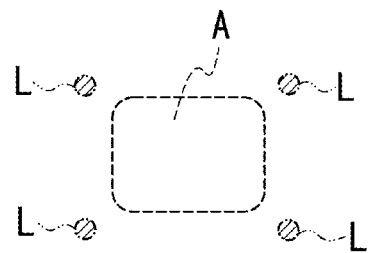

The second embodiment is different from the first embodiment, in that the pointer irradiation unit 8 irradiates the sample stage 2 with a pair of visible light beams L in the first embodiment, but the pointer irradiation unit 8 irradiates the sample stage 2 with four visible light beams L as illustrated in FIG. 4 and FIGS. 5A and 5B in the X-ray fluorescence analyzer according to the second embodiment. That is, in the second embodiment, the pointer irradiation unit 8 includes four laser beam irradiation mechanisms 8a and is set to irradiate the vicinities of four corners or four sides of the field-of-view area A with the visible light beams L.

The four laser beam irradiation mechanisms 8a are installed around the imaging unit 6 so as to surround the imaging unit 6 and are disposed to irradiate the vicinities of four sides of the field-of-view area A having a substantially-rectangular shape with the visible light beams L, for example, as illustrated in FIG. 5A. As illustrated in FIG. 5B, the four laser beam irradiation mechanisms 8a may be disposed to irradiate the vicinities of four corners of the field-of-view area A having a substantially-rectangular shape with the visible light beams L.

In this way, in the X-ray fluorescence analyzer according to the second embodiment, since the pointer irradiation unit 8 irradiates the vicinities of four corners or four sides of the field-of-view area A having a substantially-rectangular shape with the visible light beams L, the field-of-view area A having a substantially-rectangular shape is surrounded by four visible light beams L and it is thus possible to easily understand the position and the size of the field-of-view area A.

Figure 6:
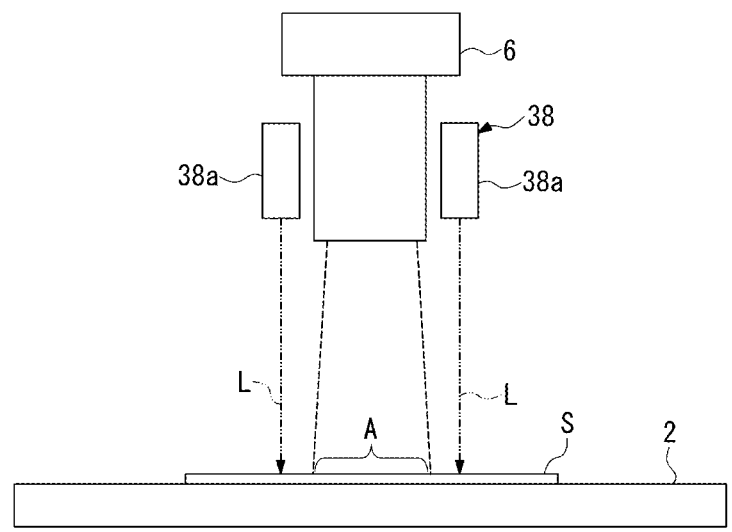
FIG. 6 is a front view illustrating an imaging unit, a pointer irradiation unit, and a sample stage in an X-ray fluorescence analyzer and a measurement position adjusting method thereof according to a third embodiment of the disclosure.
Figure 7:
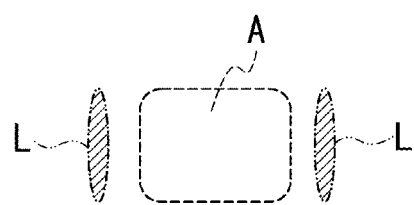
FIG. 7 is a plan view illustrating a positional relationship between a field-of-view area and visible light in the third embodiment.

The third embodiment is different from the first embodiment, in that the pointer irradiation unit 8 irradiates the sample stage 2 with the visible light beams L in a dot shape in the first embodiment, but a pointer irradiation unit 38 irradiates the sample stage 2 with the visible light beams in a substantially linear shape along at least a part of the outer circumference of the field-of-view area A as illustrated in FIGS. 6 and 7 in the X-ray fluorescence analyzer according to the third embodiment. That is, in the third embodiment, the vicinities of both sides of the rectangular field-of-view area A are irradiated with visible light beams L having substantially linear shapes along both sides of the rectangular field-of-view area A as illustrated in FIG. 7.

Each laser beam irradiation mechanism 38a of the pointer irradiation unit 38 is set to shape a visible laser beam into an elliptical shape having a major axis much longer than a minor axis using an optical system such as a lens and to irradiate the sample stage 2 with a visible light beam L having a substantially-linear shape. Particularly, the length of the visible light beam L having a substantially linear shape is set to be equal to the length of an opposed side of the field-of-view area A.

In this way, in the X-ray fluorescence analyzer according to the third embodiment, since the visible light beam L has a substantially-linear shape along at least a part of the outer circumference of the field-of-view area A, it is easy to understand the outer circumference of the field-of-view area A based on the visible light beam L having a substantially-linear shape with which the sample stage 2 has been irradiated.

The scope of the present disclosure is not limited to the above-described embodiments, and the disclosure can be modified in various forms without departing from the spirit of the present disclosure.

For example, in the above-described embodiments, the present invention is applied to an energy-dispersion type X-ray fluorescence analyzer that measures energy and intensity of X-rays using a pulse height analyzer. However, the present invention may be applied to a wavelength-dispersion type X-ray fluorescence analyzer that disperses fluorescent X-rays using a dispersive crystal and measures a wavelength and intensity of the X-rays.

A laser beam is employed as a visible light beam in the above-mentioned embodiments, but spotlight may be employed.

The units mainly configuring the X-ray fluorescence analyzer 1 such as the X-ray source, the detector, and the imaging unit are disposed above the sample stage in FIG. 1, but may be disposed below the sample stage to analyze and measure a bottom side of a sample. The detector may be of a vacuum tube type or the like. The sample stage is set to be movable in the planar directions, but may be of a fixed type which is not movable in the planar directions.

According to the present disclosure, the following advantages can be obtained.

That is, in the X-ray fluorescence analyzer and the measurement position adjusting method therefore according to the disclosure, since the pointer irradiation unit irradiates an area in the vicinity of the field-of-view area of the sample stage, which is an area other than the field-of-view area displayed on the display unit, with visible light, it is possible to perform the coarse positioning operation using the visible light with which the sample stage is irradiated as a mark. Thereafter, in the fine positioning operation, since the visible light does not appear in the field-of-view area displayed on the screen of the display unit, an image of a sample surface without a degradation in image quality or an interference with visible light is displayed. Accordingly, it is possible to perform the fine positioning operation without stress while watching an image captured by the imaging unit on the display unit.

What is claimed is:

1. An X-ray fluorescence analyzer comprising:
   a sample stage on which a sample subjected to an analysis is mounted;
   an X-ray source configured to irradiate the sample with primary X-rays;
   a detector configured to detect fluorescent X-rays emitted from the sample irradiated with the primary X-rays;
   an imaging unit configured to capture an image of a predetermined field-of-view area on the sample stage;
   a display unit configured to display the predetermined field-of-view area of the image captured by the imaging unit; and
   a pointer irradiation unit configured to irradiate the sample stage with a visible light at an irradiation position within an area that is outside the predetermined field-of-view area and near the predetermined field-of-view area.

2. The X-ray fluorescence analyzer according to claim 1, wherein the pointer irradiation unit emits a laser beam as the visible light.

3. The X-ray fluorescence analyzer according to claim 1, wherein the pointer irradiation unit irradiates the sample stage with the visible light at a first irradiation position near a first edge of the predetermined field-of-view area and at a second irradiation position near a second edge of the predetermined field-of-view area, the second edge being opposite the first edge.

4. The X-ray fluorescence analyzer according to claim 1, wherein the imaging unit is configured to be capable of changing a size of the predetermined field-of-view area, and
   wherein the pointer irradiation unit is configured to be capable of changing the irradiation position of the visible light in accordance with the size of the predetermined field-of-view area.

5. The X-ray fluorescence analyzer according to claim 1, wherein the visible light has a substantially-linear shape along at least a part of the outer circumference of the predetermined field-of-view area.

6. The X-ray fluorescence analyzer according to claim 1, wherein the predetermined field-of-view area has a substantially-rectangular shape, and
   wherein the pointer irradiation unit irradiates the sample stage with the visible light at four irradiation positions near four corners or four side edges of the predetermined field-of-view area.

7. A measurement position adjusting method for an X-ray fluorescent analyzer of capturing an image of a sample mounted on a sample stage using an imaging unit, displaying the image captured by the imaging unit on a display unit, positioning X-rays with which the sample is irradiated, and performing measurement or analysis of the sample, the method comprising:
   coarsely positioning the sample while irradiating the sample stage with a visible light at an irradiation position within an area that is outside a field-of-view area and near the field-of-view area;
   displaying the image captured by the imaging unit on the display unit; and
   finely positioning the sample based on the image displayed on the display unit after coarsely positioning the sample.

8. The measurement position adjusting method according to claim 7, further comprising:
   changing a size of the field-of-view area, and
   changing the irradiation position of the visible light in accordance with the size of the field-of-view area.

9. A measurement position adjusting method for an X-ray fluorescence analyzer having a sample stage, an imaging unit and a display unit, the method comprising:
   coarsely positioning a sample mounted on the sample stage while irradiating the sample stage with a visible light at an irradiation position within an area that is outside a field-of-view area and near the field-of-view area, the field-of-view area being an area on the sample stage in which an image is captured by the imaging unit;
   capturing the image of the field-of-view area by the imaging unit;
   displaying the image captured by the imaging unit on the display unit; and
   finely positioning the sample based on the image displayed on the display unit after coarsely positioning the sample.

10. The measurement position adjusting method according to claim 9, further comprising:
    changing a size of the field-of-view area, and
    changing the irradiation position of the visible light in accordance with the size of the field-of-view area.

* * * * *